US00PP08313P

United States Patent [19]

Vletter

[11] Patent Number: Plant 8,313

[45] Date of Patent: Jul. 20, 1993

[54] LILY PLANT NAMED ACAPULCO

[75] Inventor: Floris Vletter, Rijnsburg, Netherlands

[73] Assignee: Gebr. Vletter & J.A. Den Haan, Rijnsburg, Netherlands

[21] Appl. No.: 796,693

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct cultivar of lily plant named Acapulco, characterized by its intense and distinctive pink flower color with deeper red streading along the midvein, numerous very dark pink spot markings concentrated in center, upright-oriented flowers, and its long flower stems.

1 Drawing Sheet

The present invention comprises a new and distinct cultivar of lily, botanically known as Lilium, known commerically as Lilium oriental hybrid, and hereinafter referred to by the cultivar name Acapulco. The parents were oriental varieties belonging to divison VII(b) described in "Classification of Lily Cultivars into Divisions" published by Victoria Mathews, The Royal Botanic Gardens, Kew (1989).

The new cultivar is a product of a planned breeding program which had the objectives of creating new lily cultivars with upright flowers, good forcing habits, and soft purple flower color.

The new cultivar was originated from a hybridization made by the inventor in a controlled breeding program in Rijnsburg, The Netherlands in 1981. The female parent was the cultivar Stargazer, and the male parent was an unnamed seedling.

The new cultivar was discovered and selected as one flowering plant within the progeny of the stated cross by the inventor in July 1981 in a controlled environment in Rijnsburg, The Netherlands.

The first act of asexual reproduction of the new cultivar was accomplished by the inventor when scales were taken from the initial selection in 1985 in a controlled environment in Rijnsburg, The Netherlands.

Horticultural examination of selected units has demonstrated that the combination of characteristics as herein disclosed for Acapulco are firmly fixed and are retained through successive generations of asexual reproduction.

The new cultivar has not been observed under all possible environmental conditions. The phenotype may vary somewhat with variations in environment such as temperature, light intensity, and day length, without, however, varying the genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Intense and distinctive lilac pink flower color;
2. Very dark spot markings;
3. The midveins of the flowers are a deeper reddish pink;
4. Flowers are oriented in an upright position;

5. Flowers are carried on relative long stems.

Of the many commercial cultivars known to the present inventor, the most similar in comparision to the new cultivar is the female parent Stargazer. In comparison to Stargazer, Acapulco has a distinctive lilac flower color and longer flower stems. When flowering is forced under natural light, Acapulco produces an inflorescence approximately 14 days earlier than Stargazer, grown under the same conditions. Acapulco is fertile.

The accompanying photographic drawing shows typical flower characteristics of the new cultivar, with colors being as true as possible with illustrations of this type. The photo comprises a front elevational view of several flowers and buds at various stages.

In the following description, color references are made to The Royal Horticultural Society (R.H.S.) Colour Chart. The color values were determined at Wageningen in 1988–1989 and at Rijnsburg in July 1991.

Origin: Seedling from Breeding Program.

Parentage:
- Seed parent: Stargazer.
- Pollen parent: Unnamed seedling.

Classification:
- Botanical: Lilium.
- Commercial: Oriental hybrid.

THE PLANT

Form: A single stem carrying numerous pedicels alternately arranged.

Height: Approximately 130 cm at time of opening of anthers of first flower.

Growth habit: Vigorous.

Stem: Circular in transverse section, approximately 2 cm in thickness; anthocyanin pigmentation (185C) present; stem color 144B.

Foliage:
- *Quantity.*—35–45 leaves depending on growing conditions.
- *Size of leaf.*—Mature leaves are of medium length, 16 cm; width medium to wide, 4.5 cm.
- *Shape of leaves.*—Elliptical.
- *Texture.*—Smooth with almost no glossiness.
- *Color.*—Medium green 137A.

Bulbs:
- *Size.*—Outlet 6–30 cm.
- *Color.*—Purplish brown.

Roots: Both stem and contractile present.

THE BUD

Form: Tapering (like a lancet).
Size: 12.5 cm.
Opening; Unfolds normally.
Color: 63C prior to opening.
Tepals: Folded, three visible.

THE FLOWER

Blooming habit: Raceme.
Size: Approximately 24 cm in diameter, depending on growing conditions.
Borne: Upright to horizontal.
Shape: Generally in form of hexagonal star; bowl-shaped in cross section.
Tepalage:
*Number of tepals.*—Six.
*Arrangement.*—Three inner and three outer eack with marginal undulation.
Color.—Upper surface: Light purple 63B-C, with deeper red-purple streaking along the midvein. Lower surface: Light purple 63C.
*Spotting or marking.*—Very dark pink spots; concentrated in center, each approximately 2 mm in diameter; yellow to green colored strip at base of each tepal.
Nectaries and papillae; Present; very strong.

Pedicel:
*Length.*—10 cm (the first, flower).
*Color.*—Medium green with anthocyanin on the upper side.
*Form.*—Largely curved.
Texture: Papillose.
Disease resistance: No disease problems noted to date.
Fragrance: Present; weak.
Lasting quality: Excellent.

REPRODUCTIVE ORGANS

Stamens, anthers:
*Arrangement.*—Anthers form a generally circular pattern.
*Length.*—Medium, 8 cm.
*Number.*—Six.
*Filaments.*—Light green.
Pollen color: Light brown to orange brown.
Anther color: Purple.
Pistils: One green style; total length of pistil 10.5 cm.
Stigma: Triangular; purple to dark purple.
Ovaries: Triangular in shape; other characteristics typical of oriental lily varieties.

I claim:

1. A new and distinct cultivar of lily plant named Acapulco, as illustrated and described.

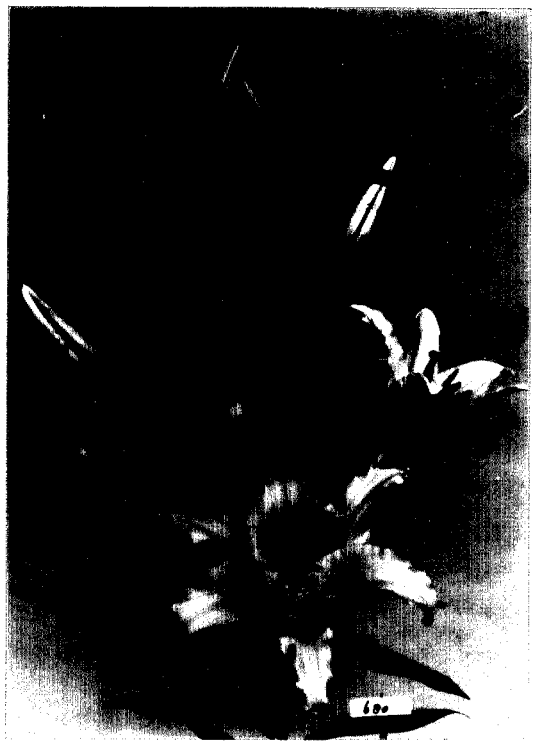

* * * * *